United States Patent [19]

Brand

[11] 4,238,424
[45] Dec. 9, 1980

[54] PROCESS FOR S-CHLOROMETHYLATION OF ORGANIC DITHIOPHOSPHO COMPOUNDS WITH METHYLENE CHLORIDE

[75] Inventor: William W. Brand, Painesville, Ohio

[73] Assignee: Diamond Shamrock Corporation, Dallas, Tex.

[21] Appl. No.: 53,066

[22] Filed: Jun. 28, 1979

[51] Int. Cl.³ ............................................. C07F 9/165
[52] U.S. Cl. ..................................... 260/979; 260/963
[58] Field of Search ........................................ 260/979

[56] References Cited

U.S. PATENT DOCUMENTS

| | | | |
|---|---|---|---|
| 3,014,058 | 12/1961 | Willard et al. | 260/979 |
| 3,020,304 | 2/1962 | Scherer et al. | 260/979 |
| 3,641,223 | 2/1972 | Schlor et al. | 260/979 |
| 3,660,543 | 5/1972 | Mueller et al. | 260/979 |
| 3,896,219 | 7/1975 | Pianka | 424/222 |

Primary Examiner—Anton H. Sutto
Attorney, Agent, or Firm—Arthur S. Collins

[57] ABSTRACT

An economical process for the controlled S-chloromethylation of O-alkyl esters of dithiophospho acid compounds with methylene chloride is provided by conducting the reaction in a liquid medium comprising a large excess of methylene chloride and a substantial, reaction promoting proportion of a highly polar, miscible, organic cosolvent.

20 Claims, No Drawings

PROCESS FOR S-CHLOROMETHYLATION OF ORGANIC DITHIOPHOSPHO COMPOUNDS WITH METHYLENE CHLORIDE

INTRODUCTION

This invention is concerned with methods for preparing S-chloromethyl derivatives of lower alkyl esters of dithiophospho acids such as O,O-dialkyl dithiophosphoric acids and O-alkyl, alkyl dithiophosphonic acids. Such derivatives are of commercial interest typically because of their biological activity (e.g., insecticidal properties) and, additionally, because of their capability to serve as useful intermediates in synthesizing other active functional compounds.

BACKGROUND OF THE INVENTION

The production of S-chloromethyl derivatives of organic dithiophospho acid compounds has suffered economic disadvantages due to the erratic nature of the S-chloromethylation reaction and difficulties in conducting this reaction on a sustained basis to give a high yield of a relatively pure product. Indeed, in order to attain adequate reactivity in a practical production process, the prior art has resorted to the use of a rather expensive chloromethylating agent, namely, bromochloromethane.

Exemplary of the prior art are U.S. Pat. Nos. 3,020,304 (Scherer et al.) and 3,896,219 (Pianka), both of which exclusively employ bromochloromethane as the chloromethylating reagent. The reaction conditions utilized by said patentees are quite similar, with reaction temperatures generally below 100° C. and the usual addition of some inert solvents such as alcohols and ketones. The best results achieved by the two patentees also appear to be quite comparable since Example 2 of U.S. Pat. No. 3,020,304 indicates a yield of about 70 percent of a dithiophosphoric acid derivative using 4 times the stoichiometric proportion of bromochloromethane while U.S. Pat. No. 3,896,219 attained a 75 percent yield of a dithiophosphoric acid derivative using the same proportion of bromochloromethane in the experiment described in the first paragraph of column 7 thereof.

In view of the present state of this art and its virtual dependence upon a single, specialized chloromethylating reagent for practical operations, it would clearly be most desirable to have a satisfactory alternative process employing a more economical and readily available chloromethylating reagent. The present invention is directed to devising a practical process based upon the use of methylene chloride.

SUMMARY OF THE INVENTION

It has now been discovered that not only an entirely practical process but also a more economical process can be devised for making S-chloromethyl derivatives of O-alkyl esters of dithiophospho acids by utilizing methylene chloride as the chloromethylating reagent provided that a truly massive excess of same is employed, i.e., of the order of at least about 25 times the stoichiometric amount theoretically required to react with the starting dithiophospho acid compound. In addition to such massive excesses of methylene chloride, a chemically nonreacting, strongly polar cosolvent miscible with methylene chloride should also be present in significant amounts to promote reactivity and insure formation of the desired product in adequate yields.

In short, the present process comprises reacting methylene chloride with an O-alkyl ester of a dithiophospho acid salt, which is either preformed or generated in situ from the corresponding acid compound and a suitable base, in the presence of (1) a huge excess of methylene chloride in the range of about 25 to about 200 times, and preferably about 35 to about 150 times, stoichiometric, and (2) an amount of miscible, chemically nonreacting, strongly polar cosolvent which provides significant promotion of the reaction to form the corresponding S-chloromethyl derivative. In most cases, the amount of cosolvent employed will lie in the range from about 10 to 200 percent, and preferably from about 20 to about 150 percent, by volume based upon the liquid volume of said methylene chloride.

DETAILED DESCRIPTION AND PREFERRED EMBODIMENTS

The presently preferred class of S-chloromethyl derivatives are those derived from O,O-dialkyl esters of dithiophosphoric acid, particularly those where each alkyl group is a lower alkyl, e.g., of from 1 to about 4 carbon atoms. Accordingly, the preferred starting materials for the present process are salts of compounds having the following general structure:

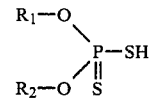

wherein each of $R_1$ and $R_2$ is a lower alkyl group, preferably of 1-4 carbon atoms. For example, O,O-diethyl dithiophosphoric acid is a most preferred individual species representative of this general structure.

The most desirable salts for use as the starting material of the instant process are the alkali metal and ammonium salts but salts of alkaline earth metals can also be employed. However, as already indicated, it makes little difference whether the salt is preformed or merely generated in situ by including a suitable base in the methylene chloride-cosolvent reaction medium.

The other extremely important factor responsible for the success of the present process is the inclusion in the reaction medium of a significant proportion of a strongly dipolar cosolvent which, at least under reaction conditions, is miscible with (or soluble in) the methylene chloride. Although the leverage delivered by a given cosolvent in promoting the desired reaction of the methylene chloride cannot be estimated quantitatively solely from numerical values of its dipolar parameters, those with high values of both dipole moment and dielectric constant are almost invariably very effective cosolvents. Especially notable, for example, are the lower carboxamides such as formamide, acetamide and propionamide and their N-lower alkyl derivatives (particularly the N-methyl and N,N-dimethyl derivatives) as well as hexamethyl phosphoramide, N-methyl pyrrolidone, dimethyl sufoxide, tetrahydrothiophene-1,1-dioxide (sulfolane) and acetonitrile. Substantially, all of the aforementioned exemplary cosolvents have dielectric constants of around 30 or higher and dipole moments above about 3. Hydrocarbons and most esters and simple acyclic ethers are not very polar and are of little or no interest as cosolvents for the present reactions.

Remaining classes of solvents such as alcohols, ketones, amines, complex ethers, polyethers and the like fall in the middle of the spectrum in regard to dipolar character. Several of such medium polar solvents are sufficiently effective to be employed in the present invention provided they are used in large enough proportions. In this intermediate category are solvents like pyridine, tetrahydrofuran, acetone, and compound ethers like glyme, diglyme, etc. (i.e., di-lower alkyl ethers of ethylene glycol or low molecule weight polyethyleneglycols). However, under most reaction conditions contemplated, the volume proportions of these intermediate cosolvents must generally be at least about equal to the methylene chloride in order to achieve attractive production rates.

The level at which such cosolvent is utilized within the broad range previously indicated (i.e., 10 to 200 percent by volume of the methylene chloride) will depend primarily on two factors, namely, the excess methylene chloride level employed and the reaction promoting potency of the particular cosolvent in question. The generally favorable range of reaction conditions of greatest practicable interest will usually involve about 20 to about 150 percent by volume of cosolvent based on methylene chloride and an excess methylene chloride level of at least about 35 and, preferably, not less than about 50, times stoichiometric.

The subject process is usually most feasible at moderately elevated reaction temperatures in the range from about 40° to about 80° C. Higher temperatures up to at least 100° C. or above can be used at many instances provided reaction conditions and times are properly controlled, and lower temperatures at least down to room temperature (about 20° C.) can be considered if production rate need not be optimized. Of course, the thermal stability of the desired product should be taken into account in order to avoid appreciable thermal decomposition thereof. Fortunately, most of the more favorable methylene chloride-cosolvent combinations used as reaction media in accordance with the teachings of this invention begin to boil under normal atmospheric pressure at temperatures close to the preferred reaction temperature range so that it is often convenient to run the process at normal pressure under liquid reflux conditions. In any case, ambient pressures are usually preferred, although, obviously, somewhat lower or higher pressures can easily by employed if desired.

Under the preferred reaction conditions described, including the use of about 35 to about 150 times the stoichiometric amount of methylene chloride and at least about 20 percent by volume of strongly dipolar cosolvent, commerically attractive conversions of the starting O,O-dialkyl esters of dithiophosphoric acid can generally be obtained in a matter of several hours (e.g., 2-24 hours). In reasonably optimized systems employing the preferred embodiments highlighted herein, yields of about 50 to about 100 percent of the desired S-chloromethylated derivatives can usually be attained based upon the starting O,O-dialkyl esterified dithiophosphoric acid, which, in salt form, reacts as follows:

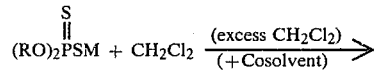

-continued

where M represents the salt forming cation.

After the desired reaction has been accomplished, most of the excess methylene chloride, being much more volatile than the strongly polar cosolvents, can be readily distilled off and recovered for reuse. After quenching the residual reaction mixture with water, the desired chloromethylated product is then extracted by means of a relatively volatile hydrocarbon solvent such as hexane, toluene, or the like. Most of the highly polar cosolvent can also be recovered for reuse by removing the water and by-product chloride salt using known techniques.

A fuller understanding of operational details and practical aspects of this invention may be had by studying the following specific experimental examples, in which the amounts of various materials specified therein are given in parts by weight unless otherwise indicated.

EXAMPLE 1

Over a period of about 15 minutes, 9.36 grams of 90 percent pure O,O-diethyl dithiophosphoric acid (0.045 mol) was gradually added to a stirred mixture of 5.3 g (0.05 mol) of sodium carbonate, 350 milliliters (5.5 mol) of methylene chloride and 150 milliliters of dimethyl formamide in a three-necked flask equipped with a thermometer and a water-cooled condenser. The reaction mixture was then heated sufficiently to effect boiling (48° C.) and maintained under liquid reflux conditions for about 22 hours. The excess methylene chloride was then removed by distillation at reduced pressures. The reaction residue remaining was cooled and worked up for product recovery by stirring same with 400 milliliters of water and extracting the aqueous mixture 3 times with hexane.

The combined hexane extract was washed twice with water and once with saturated brine and then dried with anhydrous MgSO$_4$. The hexane solvent was then distilled off leaving about 11 grams of a yellow oil. The concentration of the S-chloromethyl ester of O,O-diethyl dithiophosphoric acid in this crude product was found to be about 93 percent, by weight, based upon an nmr assay performed on a sample thereof in deuterated chloroform, involving a comparison of the integrated proton signals from the SCH$_2$Cl group at $\delta$ 4.90 (d,J=21 Hz, 2H) with the proton signals from OCCH$_3$ groups at $\delta$ 1.3 (t,J=7 Hz, 6H). This indicates that the S-chloromethyl-O,O-diethyl dithiophosphate in this experiment was produced at a calculated yield of 97 percent of theoretical. Purification was then effected by distillation of the oil at 83°-85° C. under 0.2-0.25 mm pressure.

EXAMPLE 2

The reaction of Example 1 was repeated using 1.68 grams of 90 percent pure O,O-diethyl dithiophosphoric acid (0.009 mol) and 1.1 g (0.01 mol) of sodium carbonate. The reaction time, temperature and other conditions were substantially the same, but the amount of methylene chloride used was only 20 ml or 0.31 mol (i.e., about 35 times stoichiometric instead of 122 times) and the relative proportion of dimethyl formamide to methylene chloride was also substantially less (20 percent instead of 43 percent by volume). As a result, the calculated yield of S-chloromethyl-O,O-diethyl dithiophosphate produced was reduced to about 48 percent of theoretical.

EXAMPLE 3

A mixture of 2 grams of 95 percent pure ammonium O,O-diethyl dithiophosphate (0.009 mol), 20 ml (0.31 mol) of methylene chloride and 20 ml of dimethyl formamide was heated at reflux (67° C.) for about 22 hours. After vaporizing out most of the remaining methylene chloride, the reaction mixture was cooled and worked up as in Example 1 giving 1.71 grams of a light yellow oil. The nmr analysis indicated a concentration of about 71 percent, by weight, of S-chloromethyl-O,O-diethyl dithiophosphate therein, representing an overall yield of about 54 percent of theoretical.

When this experiment was repeated using the same proportions of ammonium O,O-diethyl dithiophosphate and methylene chloride but no cosolvent, there was no visual sign of an oily product being formed, and it was confirmed by thin layer chromatography that negligible reaction of the original starting materials had occurred.

Since the refluxing temperature of methylene chloride without cosolvent present is only about 40° C., additional attempts were made to achieve the desired reaction between ammonium O,O-diethyl dithiophosphate and methylene chloride under pressure so that higher temperatures could be employed. However, even at 100° C., no reaction could be detected visually or by thin layer chromatography when using the same proportion of methylene chloride (i.e., 35 times stoichiometric) in the absence of cosolvent.

EXAMPLE 4

A mixture of 2 grams of 95 percent pure ammonium O,O-diethyl dithiophosphate (0.009 mol), 80 milliliters (1.24 mol) of methylene chloride and 20 milliliters of dimethyl formamide was heated at reflux (47° C.) for about 20 hours. After vaporizing out excess methylene chloride, the reaction mixture was cooled and worked up as in Example 1 giving 1.95 grams of a light yellow oil. The nmr analysis of a sample of this oil indicated a concentration of about 83 percent, by weight, of S-chloromethyl-O,O-diethyl dithiophosphate, representing a yield of about 74 percent of theory.

EXAMPLE 5

Using 0.009 mol of ammonium O,O-dimethyl dithiophosphate as the starting salt and duplicating the other reactants and reaction conditions of Example 4, a good yield of S-chloromethyl-O,O-dimethyl dithiophosphate is produced.

EXAMPLES 6–13

Using the procedure of Example 3 and 4, a series of 8 similar reactions between 2 grams of 95 percent pure ammonium O,O-diethyl dithiophosphate (0.009 mol) and 80 ml of methylene chloride (1.24 mol ≈ 138 times stoichiometric) was carried out using 30 ml of a different cosolvent each time. Each reaction was conducted for about 20 hours at liquid reflux conditions, and the results are summarized in Table I.

TABLE I

| Example No. | Cosolvent | Temp. | Calculated Yield |
|---|---|---|---|
| 6 | dimethyl formamide | 55° C. | 71% |

TABLE I-continued

| Example No. | Cosolvent | Temp. | Calculated Yield |
|---|---|---|---|
| 7 | dimethyl acetamide | 52° C. | 84% |
| 8 | dimethyl sulfoxide | 48° C. | 82% |
| 9 | hexamethyl phosphoramide | 50° C. | 80% |
| 10 | diglyme | 46° C. | 43% |
| 11 | pyridine | 48° C. | 34% |
| 12 | glyme | 46° C. | 20% |
| 13 | ethanol | 41° C. | 13% |

EXAMPLE 14–19

Another series of experiments was conducted with 6 different cosolvents, using the same amounts of ammonium O,O-diethyl dithiophosphate and methylene chloride as in Examples 6–13 but using 80 ml (i.e., 100 percent by volume) of cosolvent in each experiment. The results obtained from maintaining liquid reflux conditions for about 20 hours are summarized in Table II.

TABLE II

| Example No. | Cosolvent | Temp. | Calculated Yield |
|---|---|---|---|
| 14 | dimethyl formamide | 67° C. | 52% |
| 15 | acetonitrile | 47° C. | 50% |
| 16 | glyme | 56° C. | 33% |
| 17 | acetone | 53° C. | 29% |
| 18 | ethanol | 48° C. | 22% |
| 19 | tetrahydrofuran | 55° C. | 23% |

EXAMPLE 20

A mixture of 2 grams of 95 percent pure ammonium O,O-diethyl dithiophosphate (0.009 mol), 20 ml (0.31 mol) of methylene chloride and 4 ml of dimethyl formamide was sealed in glass pressure vessel which was immersed in a 100° C. oil bath for 4 hours. After removing the reactor from the bath, the contents were cooled, concentrated and processed as before to recover a yellow oily product. From the weight of this yellow oil and its nmr analysis, the yield of S-chloromethyl-O,O-diethyl dithiophosphate was calculated to be about 40 percent of theoretical.

EXAMPLE 21

A mixture of reactants as described in Example 20 was processed in the same way, except that the sealed reaction vessel was held at 150° C. for 30 minutes in this case. The resultant calculated yield of S-chloromethyl derivative was about 57 percent of theoretical.

Having disclosed the present invention clearly with the aid of exemplary embodiments thereof, it should be understood that the scope of the appended claims is intended to encompass all variations thereof which are obvious to those skilled in the art.

What is claimed is:

1. A process for preparing S-chloromethyl derivatives of O-alkyl dithiophospho acids which comprises reacting a salt thereof, which is either preformed or generated in situ by including a suitable base, with methylene chloride in the presence of:
    (1) a large excess of methylene chloride amounting to at least about 25 times stoichiometric, and
    (2) a miscible, highly polar cosolvent in amounts which effectively promote reaction by methylene chloride to form said S-chloromethyl derivatives.

2. A process as in claim 1 wherein said salt is a salt of an O,O-dialkyl dithiophosphoric acid each alkyl group in which contains 1-4 carbon atoms.

3. A process as in claim 2 wherein said salt is an ammonium or alkali metal salt.

4. A process as in claim 2 wherein said excess of methylene chloride amounts to between about 35 and about 150 times the stoichiometric amount.

5. A process as in claim 2 wherein the proportion of said miscible cosolvent is between about 10 and 200 percent by volume of said methylene chloride.

6. A process as in claim 5 wherein said miscible cosolvent is a chemically nonreacting organic compound.

7. A process as in claim 6 wherein said miscible cosolvent is from the group consisting of lower carboxamides and their N-lower alkyl derivatives, hexamethyl phosphoramide, N-methyl pyrrolidone, dimethyl sulfoxide, tetrahydrothiophene-1,1-dioxide and acetonitrile.

8. A process as in claim 2 wherein said reaction is conducted at temperatures between about 20° and about 100° C.

9. A process as in claim 8 wherein said temperatures are predominantly in the range from about 40° to about 80° C.

10. A process as in claim 8 wherein said reaction is conducted under substantially atmospheric pressure with boiling of the mixture under liquid reflux conditions.

11. A process for preparing S-chloromethyl derivatives of O,O-dialkyl dithiophosphoric acids corresponding to the formula

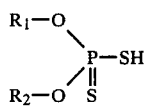

wherein each of $R_1$ and $R_2$ is a lower alkyl group of 1-4 carbon atoms comprising reacting at a temperature of between about 20° and about 100° C., a salt thereof, which is either preformed or generated in situ by including a suitable base, with an excess of methylene chloride of at least about 35 times the proportion theoretically needed for stoichiometric reaction, together with about 20 to about 200 percent by volume (based upon the liquid volume of said methylene chloride) of a miscible, chemically nonreacting, highly polar organic cosolvent.

12. A process as in claim 11 wherein said organic cosolvent is from the group consisting of lower carboxamides and their N-lower aklyl derivatives, hexamethyl phosphoramide, N-methyl pyrrolidone, dimethyl sulfoxide, tetrahydrothiophene-1,1-dioxide and acetonitrile.

13. A process as in claim 12 wherein said cosolvent in N,N-dimethyl formamide or dimethyl sulfoxide.

14. A process as in claim 11 wherein each of $R_1$ and $R_2$ is ethyl.

15. A process as in claim 11 wherein said organic cosolvent is used in proportions of about 20-150 percent by volume based upon the methylene chloride.

16. A process as in claim 11 wherein said salt is an ammonium or alkali metal salt.

17. A process as in claim 11 wherein said reaction is carried out at temperatures in the range from about 40° to about 80° C.

18. A process as in claim 11 wherein said reaction is conducted under liquid reflux conditions at about ordinary atomspheric pressure.

19. A process as in claim 11 wherein the amount of methylene chloride is at least about 50 times stoichiometric.

20. A process as in claim 11 wherein, at the end of said reaction, most of the excess methylene chloride is distilled off and recovered for reuse.

* * * * *